US012667622B2

(12) United States Patent
Livney et al.

(10) Patent No.: US 12,667,622 B2
(45) Date of Patent: *Jun. 30, 2026

(54) COMPOSITION AND METHOD FOR A PREBIOTIC DELIVERY SYSTEM TARGETED TO PROBIOTIC BACTERIA

(71) Applicant: TECHNION RESEARCH & DEVELOPMENT FOUNDATION LIMITED, Haifa (IL)

(72) Inventors: Yoav D. Livney, Misgav (IL); Adi Seifert, Karmiel (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 348 days.

This patent is subject to a terminal disclaimer.

(21) Appl. No.: 16/645,892

(22) PCT Filed: Sep. 9, 2018

(86) PCT No.: PCT/IL2018/051019
§ 371 (c)(1),
(2) Date: Mar. 10, 2020

(87) PCT Pub. No.: WO2019/049157
PCT Pub. Date: Mar. 14, 2019

(65) Prior Publication Data
US 2020/0276321 A1 Sep. 3, 2020

Related U.S. Application Data

(60) Provisional application No. 62/556,437, filed on Sep. 10, 2017.

(51) Int. Cl.
*A61K 47/61* (2017.01)
*A23L 33/21* (2016.01)
*A61K 38/40* (2006.01)
*A61K 47/64* (2017.01)
*A61K 47/69* (2017.01)

(52) U.S. Cl.
CPC ............. *A61K 47/61* (2017.08); *A23L 33/21* (2016.08); *A61K 38/40* (2013.01); *A61K 47/64* (2017.08); *A61K 47/6921* (2017.08); *A61K 47/6929* (2017.08); *A23V 2002/00* (2013.01)

(58) Field of Classification Search
None
See application file for complete search history.

(56) References Cited

U.S. PATENT DOCUMENTS

2014/0322340 A1 10/2014 Livney

FOREIGN PATENT DOCUMENTS

| CN | 106820156 A | 6/2017 |
| WO | 2012091946 A1 | 7/2012 |
| WO | 2014099134 A1 | 6/2014 |

OTHER PUBLICATIONS

Buchert et al. ("Crosslinking Food Proteins for Improved Functionality" Annu. Rev. Food Sci. Techonol. 2010, 1:113-38).*
Patel et al. (The current trends and future perspectives of prebiotics research: a review 3 Biotech (2012) 1 115-125).*
Manninen (Nutrition & Metabolism 2009,6:38).*
Raikos et al. ("Health-promoting properties of bioactive peptides derived from milk proteins in infant food: a review" Dairy Sci & Technol. (2014) 94:91-101).*
Muthaiyan et al. ("Hydolyzed Caseinomacropeptide conjugated galactooligosaccharides support the growth and enhance the bile tolerance in lactobacillus strains" Journal of Agriculture and Food Chemistry, Jun. 2012).*
Hernandez-Hernandez et al. (Proteomics, 2010, 10, 3699-3711).*
Boger et al. (J Agric Food Chem, Dec. 18, 2019; 67/50);13969-13977).*
Mukhopadhya et al. ("Milk Proteins: Processing of Bioactive Fractions and Effects on Gut Health" Milk Proteins-From Structure to Biological Properties and Health Aspects, Sep. 2016).*
W. H. Holzapfel et al., "Overview of gut flora and probiotics", Int J Food Microbiol, vol. 41 Issue 2 pp. 85-101, 1998.
Harry J. Flint et al., "The role of the gut microbiota in nutrition and health", Nat Rev Gastroenterol Hepatol, vol. 9 Issue 10 pp. 577-589, 2012.
R. A. Rastall, "Bacteria in the gut: friends and foes and how to alter the balance", J Nutr, vol. 134 Suppl 8 pages 2022S-2026S, 2004.
Taylor C. Wallace et al., "Human gut microbiota and its relationship to health and disease", Nutr Rev, vol. 69 Issue 7 pp. 392-403, 2011.
Glenn R. Gibson et al., "Dietary modulation of the human colonic microbiota: updating the concept of prebiotics", Nutr Res Rev, vol. 17 Issue 2 pp. 259-275, 2004.
Guidelines for the Evaluation of Probiotics in Food. Report of a Joint FAO/WHO Working Group on Drafting Guidelines for the Evaluation of Probiotics in Food. London Ontario, Canada. 2002.
Maria José Martin et al., "Microencapsulation of bacteria: A review of different technologies and their impact on the probiotic effects", Innov Food Sci Emerg Technol, vol. 27 pp. 15-25, 2015.
P. Marteau and B. Flourie, "Tolerance to low-digestible carbohydrates: symptomatology and methods", Br J Nutr, vol. 35 Suppl 1 pp. S17-21, 2001.

(Continued)

*Primary Examiner* — Tara L Martinez
(74) *Attorney, Agent, or Firm* — The Roy Gross Law Firm, LLC; Roy D. Gross

(57) ABSTRACT

Provided herein is a particle made of a protein covalently bound to a prebiotic carbohydrate, thereby forming a conjugate, wherein at least two said conjugates are covalently crosslinked via their carbohydrate units (e.g. by a phospho-di-ester bond). The said particle may be used for selectively promoting probiotic bacteria growth in the colon and may be used to deliver additional probiotic growth factors, or other bioactives and drugs to the colon. Furthermore, provided herein are methods for preparing the particle, and for delivering a substance bound to, or entrapped within the particle, into the gastrointestinal tract of a subject in need thereof.

11 Claims, 3 Drawing Sheets

(56)                    References Cited

OTHER PUBLICATIONS

Arthur C. Ouwehand et al. "Prebiotics and other microbial substrates for gut functionality", Curr Opin Biotechnol vol. 16 Issue 2 pp. 212-217, 2005.

Cornelia Liepke et al., "Human milk provides peptides highly stimulating the growth of bifidobacteria", Eur J Biochem vol. 269 Issue 2 pp. 712-718, 2002.

Karina Pokusaeva et al., "Carbohydrate metabolism in Bifidobacteria". Genes Nutr, vol. 6 Issue 3 pp. 285-306, 2011.

Daniel Garrido et al., "Utilization of galactooligosaccharides by Bifidobacterium longum subsp. infantis isolates", Food Microbiol, vol. 33 Issue 2 pp. 262-270, 2013.

Ganzle MG. Galacto-Oligosaccharides, In Fuquay, JW (ed.), Encyclopedia of Dairy Sciences 2nd ed. Elsevier Ltd. vol. 3, p. 209-216. 2011.

Antonio Alberto Zuppa et al, "Prebiotics and Probiotics in Infant Nutrition", In Book Probiotics, Prebiotics, and Synbiotics, pp. 101-134, 2016.

Paolo Manzoni, "Clinical Benefits of Lactoferrin for Infants and Children", J Pediatr, vol. 173 Suppl S43-S52, 2016.

P-W. Chen et al, "Antimicrobial potential for the combination of bovine lactoferrin or its hydrolysate with lactoferrin-resistant probiotics against foodborne pathogens", J Dairy Sci, vol. 96 Issue 3 pp. 1438-1446, 2013.

Kearney N, Stanton C, Desmond C, Coakley M, Collins JK, Fitzgerald G, Ross RP. Culturing of bifidobacteria, In Farnworth, ER (ed.), Handbook of Fermented Functional Foods, 2nd ed. CRC Press, pp. 37-39, 2008.

Mans Minekus et al., "A standardised static in vitro digestion method suitable for food—an international consensus", Food and Function, vol. 5 Issue 6 pp. 1113-1124, 2014.

Tatsuya Masuko et al., "Carbohydrate analysis by a phenol-sulfuric acid method in microplate format", Anal Biochem, vol. 339 Issue 1 pp. 69-72, 2005.

Oliver H. Lowry et al., "Protein measurement with the Folin phenol reagent", J Biol Chem, vol. 193 Issue 1 pp. 265-275, 1951.

María Luz Sanz et al: "Characterization and in Vitro Digestibility of Bovine [beta]-Lactoglobulin Glycated with Galactooligosaccharides", J. Agric. Food Chem. 2007, 55, 7916-7925.

Alice M. Moscovici et al: "The impact of the Maillard reaction on the in vitro proteolytic breakdown of bovine lactoferrin in adults and infants", Food Funct., 2014, 5, 1898.

Fabiola Cristina de Oliveira et al: "Food Protein-Polysaccharide Conjugates obtained via the Maillard Reaction: A Review", Critical reviews in food science and nutrition, vol. 56, No. 7, May 13, 2014, pp. 1108-1125.

Li, Y., Zhong, F., Ji, W., Yokoyama, W., Shoemaker, C.F., Zhu, S. and Xia, W., 2013. Functional properties of Maillard reaction products of rice protein hydrolysates with mono-, oligo-and polysaccharides. Food Hydrocolloids, 30(1), pp. 53-60.

Peled, S. and Livney, Y.D., 2021. Oligosaccharide-lactoferrin shell-crosslinked particles for selective targeting of proteins to probiotic bacteria in the colon. Food Hydrocolloids, 120, p. 106973.

Castanys-Muñoz, E., Martin, M.J. and Prieto, P.A., 2013. 2'-fucosyllactose: an abundant, genetically determined soluble glycan present in human milk. Nutrition reviews, 71(12), pp. 773-789. doi: 10.1111/nure.12079. Epub Nov. 18, 2013. PMID: 24246032.

Hernandez-Hernandez, O., Lebron-Aguilar, R., Quintanilla-Lopez, J.E., Sanz, M.L. and Moreno, F.J., 2010. Development of a new method using HILIC-tandem mass spectrometry for the characterization of O-sialoglycopeptides from proteolytically digested caseinomacropeptide. Proteomics, 10(20), pp. 3699-3711. doi: 10.1002/pmic.201000156. PMID: 20859957.

Manninen, A.H., 2009. Protein hydrolysates in sports nutrition. Nutrition & metabolism, 6(1), p. 38. doi: 10.1186/1743-7075-6-38. PMID: 19785737; PMCID: PMC2761917, 5pp.

Weichert, S., Jennewein, S., Hüfner, E., Weiss, C., Borkowski, J., Putze, J. and Schroten, H., 2013. Bioengineered 2'-fucosyllactose and 3-fucosyllactose inhibit the adhesion of Pseudomonas aeruginosa and enteric pathogens to human intestinal and respiratory cell lines. Nutrition research, 33(10), pp. 831-838. doi: 10.1016/j.nutres.2013.07.009. Epub Aug. 13, 2013. PMID: 24074741.

Kreuß, M., Strixner, T. and Kulozik, U., 2009. The effect of glycosylation on the interfacial properties of bovine caseinomacropeptide. Food Hydrocolloids, 23(7), pp. 1818-1826. https://doi.org/10.1016/j.foodhyd.2009.01.011.

* cited by examiner

COMPOSITION AND METHOD FOR A PREBIOTIC DELIVERY SYSTEM TARGETED TO PROBIOTIC BACTERIA

CROSS-REFERENCE TO RELATED APPLICATIONS

This application is a National Phase of PCT Patent Application No. PCT/IL2018/051019 having International filing date of Sep. 9, 2018, which claims the benefit of priority of U.S. Provisional Patent Application No. 62/556, 437, filed on Sep. 10, 2017. The contents of the above applications are all incorporated by reference as if fully set forth herein in their entirety.

FIELD OF THE INVENTION

The present invention is in the field of prebiotics.

BACKGROUND OF THE INVENTION

The human gut microbiota has long been known for its importance to gut health. The majority of the human gut microbiome is colonizing the distal gut, with about $10^{12}$ microbial cells per gram of wet feces, with great diversity of species in the adult gut. Human health is greatly affected by the human gut microbiota, which is involved with various substantial functions: supplying the host with nutrients, supporting digestion of complex foods, preventing invasion of pathogens by competition, by maintaining a barrier and by promoting immune homeostasis. One of the most influential factors on both human health and performance of the gut microbiota is the diet. Depending on our dietary intake, the gut microbiota can produce either advantageous compounds that provide protection against host disease, or adverse compounds associated with human disease. In a healthy gastrointestinal tract, which is partially colonized by probiotic bacteria (naturally symbiotic bacteria which confer benefits to the host) such as bifidobacteria and lactobacilli, the probiotics can inhibit pathogen overgrowth and entry to host cells. These microorganisms are believed to exert biological effects through a phenomenon known as colonization resistance, whereby the indigenous anaerobic flora limits the concentration of potentially pathogenic (mostly aerobic) flora in the digestive tract. Other modes of action, such as supplying enzymes or influencing enzyme activity in the gastrointestinal tract, may also account for some of the other physiologic effects that have been attributed to probiotics. Gastrointestinal health strongly depends on the fermentation products of the probiotic bacteria, such as short chain fatty acids which generally promote colonic health and protection from pathogens. A disrupted homeostasis of the gut microbiota has been found to increase the risk for obesity, to increase toxin and carcinogen production, to cause intestinal putrefaction, bowel diseases, liver infections and more.

Prebiotics are indigestible food ingredients that beneficially affect host health by selectively stimulating the growth and/or activity of one or a limited number of probiotic bacteria in the colon. Prebiotics are selectively fermentable ingredients that allow specific changes, both in the composition and/or activity of the gastrointestinal microflora that confer benefits upon host wellbeing and health. For example, fructo-oligosaccharides (FOS), galacto-oligosaccharides (GOS) and lactulose.

Probiotics and prebiotics play an important role in human nutrition. The main effects attributed to selected probiotics/ prebiotic products have been proved by clinical trials, while others have been acquired on the basis of in vitro tests which require in vivo transposition in order to be validated.

The main clinical reports in the literature for the application of probiotics have been done for the treatment of infectious diseases including viral, bacterial or antibiotic associated diarrhea, relief of chronic bowel inflammatory diseases, immuno-modulation, lowering of serum cholesterol, decreased risk of colon cancer, improve lactose digestion, reduce allergies, and effect on intestinal microbiota. Although the extensive investigation of the health benefits, information on probiotic species, a specific strain-therapeutic application, and sufficient dosages, is not sufficiently studied to allow practical and rational consumption. The limitation of ingesting probiotics, whether in functional foods or in dietary supplements, is their low survival during the manufacturing process (high temperature and shear), storage (moisture, temperature, oxygen), and transit through the gastrointestinal tract (low pH in the stomach and bile salts in the small intestine). Some of these issues are dealt with by microencapsulation of the probiotics, though this raises their cost and the extra processing steps may further lower viability during manufacture. Furthermore, encapsulated probiotics' particle size is considered too large for many food applications, as their grainy texture is perceptible. In addition, most of the studies indicate that modulation of the gut microbiota by oral probiotic administration only lasts for few days and therefore requires long-term daily intake to maintain. As for prebiotics, dose-related intolerance symptoms may appear after their ingestion (bloating, abdominal cramps, diarrhea), although, a daily dose of prebiotics <20 g/day is generally well tolerated. Moreover, none of the existing solutions for modulation of the gut microbiota contains a protein source. Proteins and their amino acids are an important nitrogen source for bacteria, but are relatively scarce in the gut (most amino acids are present at concentrations below 0.01 mM in the human colonic content), as most protein digestion products are absorbed in the small intestine. The digestion products of some proteins have been shown to selectively stimulate growth of probiotic gut bacteria.

SUMMARY OF THE INVENTION

According to some embodiments of the present invention, there is provided a particle comprising a plurality of conjugates, wherein each conjugate comprises a protein covalently bound to a prebiotic carbohydrate, wherein at least two of the conjugates are covalently linked via the prebiotic carbohydrate.

In some embodiments, the prebiotic carbohydrate is at least 60% indigestible by a mammal. In some embodiments, the prebiotic carbohydrate is an intestinal prebiotic-fermentation substrate.

In some embodiments, the prebiotic carbohydrate is selected from the group consisting of dietary fibers, galacto-oligosaccharide, fructo-oligosaccharide, inulin, resistant starch, raffinose, lactulose, stachyose, verbascose, transgalactosylated oligosaccharides, isomalto-oligosaccharides, pyrodextrins, soy-oligosaccharides, pectic-oligosaccharides, xylo-oligosaccharides, levans, synthetic or isolated mammalian milk oligosaccharides, and any combination thereof.

In some embodiments, the covalent bond is via a primary amine of the protein to a carbonyl of the carbohydrate. In some embodiments, at least two conjugates are covalently linked via a phospho-di-ester bond between a carbohydrate of a first conjugate and a carbohydrate of a second conjugate.

In some embodiments, the protein is selected from, without being limited thereto, a whole protein, and a protein hydrolysate, and any combination thereof. In some embodiments, the protein is selected from, without being limited thereto, an animal protein, a plant protein, an algal protein and a microbial protein, and any combination thereof. In some embodiments, the protein selected from, without being limited thereto, a milk protein, a lactoferrin, a transferrin, and a casein, and any combination thereof.

In some embodiments, the protein is a hydrolysate by a protease selected from, without being limited thereto, a gastric protease or an intestinal protease, or any combination thereof.

In some embodiments, the average size of a diameter of the particle is in the range of 10 nm to 3000 nm.

In some embodiments, the weight ratio of the protein to the carbohydrate in the particle is in the range of 1:10 to 10:1, respectively.

In some embodiments, the particle comprises a core and shell, wherein the core comprises at least 80% by weight of the protein and the shell comprises at least 80% by weight of the carbohydrate. In some embodiments, the core, the shell or both further comprises a prebiotic nutritional agent. In some embodiments, the core, the shell or both further comprises a therapeutic agent. In some embodiments, the core, the shell or both further comprises a prebiotic growth factor.

According to some embodiments of the present invention, there is provided a composition comprising a plurality of particles, as described herein, wherein the plurality of particles is in a form of a suspension. In some embodiments, the composition is in the form of an agglomerate of particles. In some embodiments, the composition in the form of a powder. In some embodiments, the composition is an oral composition.

According to some embodiments of the present invention, there is provided a method of enriching probiotic bacteria in the colon of a subject, comprising the step of administering to the subject a nutritionally or a therapeutically effective amount of the composition described herein.

According to some embodiments of the present invention, there is provided a method of delivering an agent to the gastrointestinal tract of a subject, comprising the step of administering to the subject a nutritionally or a therapeutically effective amount of the composition described herein. In some embodiments, the delivering is to a location selected from a distal gut or a colon of the subject. In some embodiments, the agent is a therapeutic agent. In some embodiments, the agent is a prebiotic nutritional agent. In some embodiments, the agent is a prebiotic growth factor.

According to some embodiments of the present invention, there is provided a process for producing the particle described herein, the process comprises: (a) covalently bonding a protein and a prebiotic carbohydrate, thereby forming a conjugate; and (b) crosslinking at least two conjugates via the carbohydrate. In some embodiments, the covalently bonding comprises contacting the protein and the carbohydrate in an aqueous solution, and incubating the solution for 0.5-5 h at 40-100° C. In some embodiments, the covalently bonding comprises contacting the protein and the carbohydrate in an aqueous solution, drying the solution, thereby forming a powder; and incubating the powder at 50-70° C. at 75-85% relative humidity for 1-72 h. In some embodiments, the crosslinking comprises providing the conjugate, adding a crosslinking compound at a pH solution of at least 8, and incubating the solution for 1-12 h at 20-50° C. In some embodiments, the crosslinking compound is selected from, without being limited thereto, sodium trimetaphosphate (STMP), monosodium phosphate (SOP), sodium tripolyphosphate (STPP), and phosphoryl chloride (POCL$_3$), or any combination thereof.

In some embodiments, the process comprises a step of hydrolyzing the protein prior to forming the conjugate, comprising: (i) contacting the protein with a protease in an aqueous solution, and (ii) incubating the solution for 0.5-5 h at 25-45° C. In some embodiments, the protein is a hydrolysate of a protease selected from a gastric protease or an intestinal protease, or any combination thereof.

In some embodiments, the process further comprises a step of entrapping an agent selected from, without being limited thereto, a prebiotic growth factor, a nutraceutical, a prebiotic nutritional agent, or a therapeutic agent, or any combination thereof, comprising: contacting the compound with the conjugate prior to step (b) described herein.

In some embodiments, the weight ratio of the protein to the carbohydrate in the solution of step (a) described herein is in the range of 1:10 to 10:1, respectively.

Further embodiments and the full scope of applicability of the present invention will become apparent from the detailed description given hereinafter. However, it should be understood, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The Particle

Figure 1:
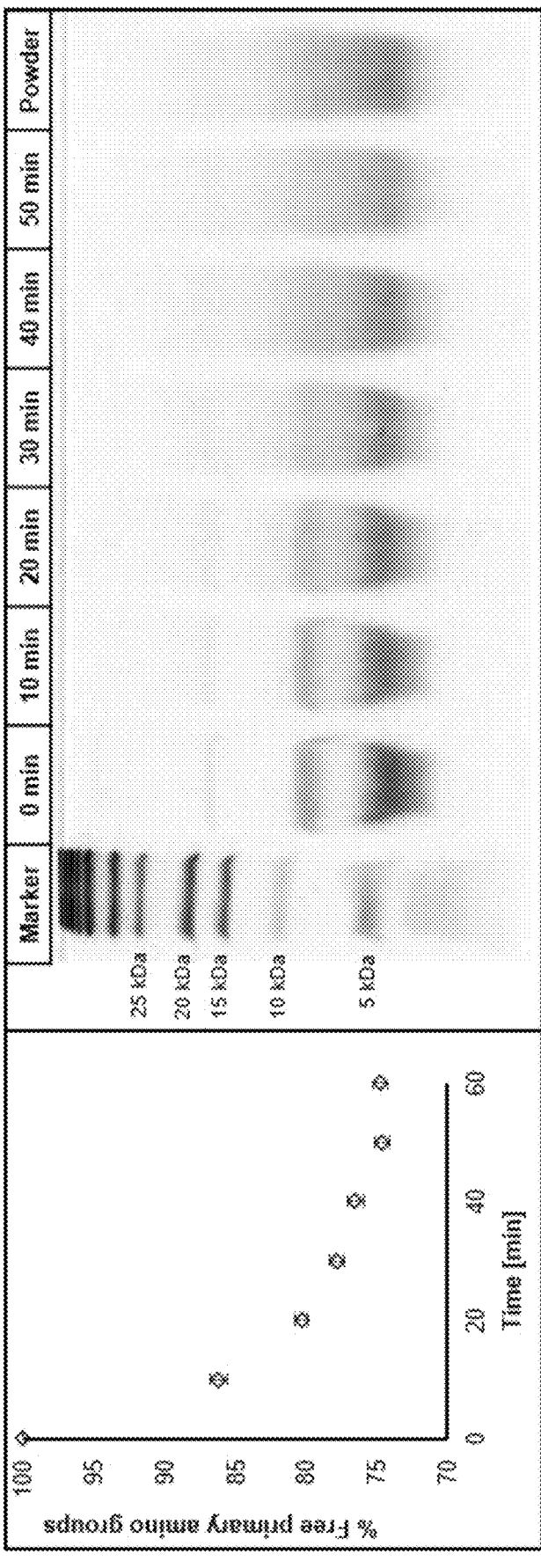
FIG. 1 depicts progression of the Maillard conjugation between galactooligosaccharides (GOS) and lactoferrin hydrolysate (LFH). Left: Percent of free primary amino groups in the LFH with Maillard reaction time, determined by the OPA assay. Right: Molecular weight distribution of the LFH-GOS particles with Maillard reaction time (0-50 min). Left lane: molecular weight size marker. Right lane: reconstituted lyophilized powder of isolated LFH-GOS conjugates.

According to some embodiments of the present invention, there is provided a particle comprising a plurality of conjugates, wherein each conjugate comprises a protein covalently bound to a prebiotic carbohydrate unit, wherein at least two of the conjugates are covalently linked via the prebiotic carbohydrate units.

The term "unit" refers herein to a single carbohydrate molecule. In some embodiments, the "unit" comprises a monomeric, oligomeric or a polymeric carbohydrate. In some embodiments, the "unit" comprises a homo-carbohydrate or a hetero-carbohydrate (i.e., comprises different monomers). In some embodiments, the covalent bond is formed between two identical "units" (i.e., a homo-crosslinking). In some embodiments, the covalent bond is formed between two different "units" (i.e., a hetero-crosslinking).

The phrase "prebiotic carbohydrate" refers to a carbohydrate, specifically a host-indigestible carbohydrate, that beneficially affects the host by selectively stimulating the growth and/or activity of one or a limited number of bacterial species in the host's colon, which provide benefits to the host.

The phrase "indigestible carbohydrate" refers to a carbohydrate which is partially digested in the gastrointestinal tract by the action of acids (e.g., gastric acid) or digestive enzymes present in the human upper digestive tract (stomach and small intestine). In some embodiments, the carbohydrate of the particle of the invention are fermented by certain types of bacteria of the human intestinal microbiota, specifically the intestinal probiotic bacteria.

In some embodiments, the prebiotic carbohydrate is an oligosaccharide. In some embodiments, the oligosaccharide has a degree of polymerization (DP) of 2 to 100. In some embodiments, the oligosaccharide has a degree of polymerization (DP) of 2-50.

In some embodiments, the carbohydrate is a modified or a non-modified carbohydrate, or any combination thereof. In some embodiments, the carbohydrate is a reducing sugar. In some embodiments, the carbohydrate is a polysaccharide. In some embodiments, the carbohydrate is an oligosaccharide.

The phrase "modified carbohydrate" refers herein to an enzymatically and/or a chemically driven covalent linkage of an organic group to the carbohydrate backbone, e.g., O-acetylation, O-sulfation, O-alkylation, and O-phosphorylation.

In some embodiments, the prebiotic carbohydrate is selected from the group consisting of dietary fibers, galacto-oligosaccharide, fructo-oligosaccharide, inulin, resistant starch, raffinose, lactulose, stachyose, verbascose, transgalactosylated oligosaccharides, isomalto-oligosaccharides, pyrodextrins, soy-oligosaccharides, pectic-oligosaccharides, xylo-oligosaccharides, levans, synthetic or isolated mammalian milk oligosaccharides, and any combination thereof.

In some embodiments, the covalent bond is via a primary amine of the protein to a carbonyl of the carbohydrate. In some embodiments, at least two conjugates are covalently linked via a phospho-di-ester bond between a carbohydrate of a first conjugate and a carbohydrate of a second conjugate.

In some embodiments, the primary amine is selected from an ε-amino group of a lysine sidechain, or an α-amino group of a protein N-terminus. In some embodiments, the carbonyl is of an aldehyde group of a reducing sugar.

In some embodiments, the covalent bond between the protein and the carbohydrate is a schiff base bond. In some embodiments, the covalently bound protein and carbohydrate complex is termed as a "Maillard conjugate".

In some embodiments, the protein is a food-grade protein. In some embodiments, the protein is selected from a whole protein, and a protein hydrolysate, and any combination thereof. In some embodiments, the protein is selected from, without being limited thereto, an animal protein, (e.g., mammal), a plant protein, an algal protein, and a microbial protein, and any combination thereof. In some embodiments, the protein selected from, without being limited thereto, a milk protein, a lactoferrin, a transferrin, and a casein, and any combination thereof. In some embodiments, the transferrin is selected from, without being limited thereto, lacto-transferrin (i.e., lactoferrin or LTF), Melanotransferrin (MTF), inhibitor of carbonic anhydrase (ICA) or serotransferrin (STF). In some embodiments, the casein is selected from, without being limited thereto, alpha S1 casein, alphaS2 casein, A1 beta casein, A2 beta casein, kappa casein and gamma casein.

In some embodiments, the protein is a hydrolysate by a protease selected from, without being limited thereto, a gastric protease or an intestinal protease, or any combination thereof.

In some embodiments, the average size of the particle is in the range of 10 nm to 4000 nm. In some embodiments, the average size of the particle is in the range of 100 nm to 3000 nm. In some embodiments, the average size of the particle is in the range of 200 nm to 1500 nm.

In some embodiments, the weight ratio of the protein to the carbohydrate in the particle is in the range of 1:10 to 10:1, respectively. In some embodiments, the weight ratio of the protein to the carbohydrate in the particle is in the range of 1:1 to 10:1, respectively. In some embodiments, the weight ratio of the protein to the carbohydrate in the particle is in the range of 1:1 to 7:1, respectively. In some embodiments, the weight ratio of the protein to the carbohydrate in the particle is in the range of 2:1 to 6:1, respectively. In some embodiments, the weight ratio of the protein to the carbohydrate in the particle is in the range of 1:1 to 5:1, respectively. In some embodiments, the weight ratio of the protein to the carbohydrate in the particle is in the range of 2:1 to 5:1, respectively. In some embodiments, the weight ratio of the protein to the carbohydrate in the particle is in the range of about 3:1, respectively.

In some embodiments, the particle is a micellar particle. In some embodiments, the particle comprises a core and shell. In some embodiments, the core comprises at least 70% by weight of the protein and the shell comprises at least 70% by weight of the carbohydrate. In some embodiments, the core comprises at least 80% by weight of the protein and the shell comprises at least 80% by weight of the carbohydrate. In some embodiments, the core comprises at least 90% by weight of the protein and the shell comprises at least 90% by weight of the carbohydrate.

In some embodiments, the core, the shell or both further comprises a prebiotic nutritional agent. In some embodiments, the core, the shell or both further comprises a therapeutic agent. In some embodiments, the core, the shell or both further comprises a prebiotic growth factor.

As used herein, the term "protein" is used to refer to a polymer or an oligomer of amino acid residues. The term "protein" as used herein encompass peptides, peptidomimetics (typically including non-peptide bonds or other synthetic modifications) and the peptide analogs peptoids and semi-peptoids or any combination thereof. In another embodiment, the term "protein" apply to amino acid polymers in which one or more amino acid residue is an artificial chemical analog of a corresponding naturally occurring amino acid. In one embodiment, the particle comprises a first native protein, or fragments thereof, being bound to the carbohydrate and a second therapeutic agent being a native protein or a modified protein.

As used herein, the term "analog" includes any peptide/ protein having an amino acid sequence substantially identical to one of the sequences of the proteins specifically described herein in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. Each possibility represents a separate embodiment of the present invention.

As used herein, the phrase "conservative substitution" also includes the use of a chemically derivatized residue in place of a non-derivatized residue provided that such peptide displays the requisite function as specified herein.

In another embodiment, the term "variant" refers to a polypeptide which comprises a modification of one or more amino acids s as compared to another polypeptide. In some embodiments, the modification comprises a substitution, a deletion, and/or an insertion of one or more amino acids as compared to another polypeptide. In some embodiments, the changes may be of minor nature, such as conservative amino acid substitutions resulting in conservative amino acid substitutions that do not significantly affect the activity of the polypeptide. In some embodiments, the changes may be substitution of an amino acid molecule, resulting in an addition of a glycosylation site, thereby increasing glycosylation of the polypeptide.

Typically, the present invention encompasses derivatives of the polypeptides/proteins. The term "derivative" or "chemical derivative" includes any chemical derivative of the polypeptide having one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

In addition, a peptide/protein derivative can differ from the natural sequence of the peptide/protein described herein, by chemical modifications including, but are not limited to, terminal-NH2 acylation, acetylation, or thioglycolic acid amidation, and by terminal-carboxlyamidation, e.g., with ammonia, methylamine, and the like. Peptides can be either linear, cyclic or branched and the like, which conformations can be achieved using methods well known in the art.

The peptide/protein derivatives and analogs according to the principles of the present invention can also include side chain bond modifications, including but not limited to —CH2—NH—, —CH2-S—, —CH2-S=0, OC—NH—, —CH2-O—, —CH2-CH2-, S=C—NH—, and —CH=CH—, and backbone modifications such as modified peptide bonds. Peptide bonds (—CO—NH—) within the peptide can be substituted, for example, by N-methylated bonds (—N(CH3)-CO—); ester bonds (—C(R)H—C—O—O—C(R)H—N); ketomethylene bonds (—CO—CH2-); a-aza bonds (—NH—N(R)—CO—), wherein R is any alkyl group, e.g., methyl; carba bonds (—CH2-NH—); hydroxyethylene bonds (—CH(OH)—CH2-); thioamide bonds (—CS—NH); olefmic double bonds (—CH=CH—); and peptide derivatives (—N(R)—CH2-CO—), wherein R is the "normal" side chain, naturally presented on the carbon atom. These modifications can occur at one or more of the bonds along the peptide chain and even at several (e.g., 2-3) at the same time.

The peptide/protein analogs can also contain non-natural amino acids. Examples of non-natural amino acids include, but are not limited to, sarcosine (Sar), norleucine, ornithine, citrulline, diaminobutyric acid, homoserine, isopropyl Lys, 3-(2'-naphtyl)-Ala, nicotinyl Lys, amino isobutyric acid, and 3-(3'-pyridyl-Ala).

Furthermore, the peptide/protein analogs can contain other derivatized amino acid residues including, but not limited to, methylated amino acids, N-benzylated amino acids, O-benzylated amino acids, N-acetylated amino acids, O-acetylated amino acids, carbobenzoxy-substituted amino acids and the like. Specific examples include, but are not limited to, methyl-Ala (Me Ala), MeTyr, MeArg, MeGlu, MeVal, MeHis, N-acetyl-Lys, O-acetyl-Lys, carbobenzoxy-Lys, Tyr-O-Benzyl, Glu-O-Benzyl, Benzyl-His, Arg-Tosyl, t-butylglycine, t-butylalanine, phenylglycine, cyclohexylalanine, and the like.

The invention further includes peptide/protein analogs, which can contain one or more D-isomer forms of the amino acids. Production of retro-inverso D-amino acid peptides where at least one amino acid and perhaps all amino acids are D-amino acids is well known in the art. When all of the amino acids in the peptide are D-amino acids, and the N- and C-terminals of the molecule are reversed, the result is a molecule having the same structural groups being at the same positions as in the L-amino acid form of the molecule. However, the molecule is more stable to proteolytic degradation and is therefore useful in many of the applications recited herein. Diastereomeric peptides may be highly advantageous over all L- or all D-amino acid peptides having the same amino acid sequence because of their higher water solubility, lower immunogenicity, and lower susceptibility to proteolytic degradation. The term "diastereomeric peptide" as used herein refers to a peptide comprising both L-amino acid residues and D-amino acid residues. The number and position of D-amino acid residues in a diastereomeric peptide of the preset invention may be variable so long as the peptide/protein is capable of displaying the function of the protein disclosed in the invention.

The Composition

According to some embodiments of the present invention, there is provided a composition comprising a plurality of particles, as described herein, wherein the plurality of particles is in a form of a suspension. In some embodiments, the composition is in the form of an agglomerate of particles. In some embodiments, the composition in the form of a powder.

In some embodiments, the composition is an oral composition. In some embodiments, the oral composition is selected from, without being limited thereto, a tablet, a capsule, a syrup, a suspension, a beverage or a food product.

Oral administration, in one embodiment, comprises a unit dosage comprising a particle and/or a composition as described herein in a form comprising tablets, capsules, lozenges, chewable tablets, suspensions, emulsions and the like. Such unit dosage forms comprise a safe and effective amount of the desired therapeutic or nutraceutical compound or compounds, each of which is in one embodiment, from about 0.1-20 g, or about 1-20 gram e.g., per daily use.

In some embodiments, tablets comprising particles and/or composition as described herein further comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc.

In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. In some embodiments, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form of the present invention comprises an extended release tablets, capsules, lozenges or chewable tablets. In one embodiment, the oral dosage form of the present invention comprises a slow release tablets, capsules, lozenges or chewable tablets. In one embodiment, the oral dosage form of the present invention comprises an immediate release tablets, capsules, lozenges or chewable tablets. In one embodiment, the oral dosage form is formulated according to the desired release profile of the pharmaceutical active ingredient as known to one skilled in the art.

Peroral compositions, in some embodiments, comprise liquid solutions, emulsions, suspensions, and the like comprising a particle and/or a composition comprising a particle as described herein. In some embodiments, pharmaceutically-acceptable carriers suitable for preparation of such compositions are well known in the art. In some embodiments, liquid oral compositions comprise from about 0.012% to about 0.933% of the desired compound or compounds, or in another embodiment, from about 0.033% to about 0.7%.

In some embodiments, the composition is a pharmaceutical composition. In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, pharmaceutical compositions for use in accordance with the present invention is formulated in conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

The compositions also comprise, in some embodiments, preservatives, such as sodium sorbate, benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed.

In another embodiment, the particle and/or the composition comprising the particle as described herein can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

In another embodiment, the pharmaceutical composition delivered in a controlled release system (see, e.g., Goodson, in Medical Applications of Controlled Release, supra, vol. 2, pp. 115-138 (1984). Other controlled release systems are discussed in the review by Langer (Science 249:1527-1533 (1990).

In some embodiments, the particle and/or the composition comprising the particle as described herein is in powder form for constitution with a suitable vehicle, e.g., sterile, pyrogen-free water based solution, before use.

In one embodiment, the preparation of the present invention is formulated in rectal compositions such as suppositories or retention enemas, using, e.g., conventional suppository bases such as cocoa butter or other glycerides.

In some embodiments, pharmaceutical compositions suitable for use in context of the present invention include compositions wherein the particle and/or the composition comprising the particle as described herein are contained in an amount effective to achieve the intended purpose. In some embodiments, a therapeutically effective amount means an amount of the particle and/or the composition comprising the particle as described herein effective to prevent, alleviate or ameliorate symptoms of disease or prolong the survival of the subject being treated.

In one embodiment, determination of a therapeutically effective amount is well within the capability of those skilled in the art.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of *theobroma*; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the compound is basically determined by the way the compound is to be administered.

In addition, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

The compositions also include incorporation of the particle and/or the composition comprising the particle as described herein into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

In some embodiments, the particle and/or the composition comprising the particle as described herein is modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In one embodiment, the modifications also increase the compound's solubility in aqueous solution, eliminate aggregation, enhance the physical and chemical stability of the compound, and reduce the immunogenicity and reactivity of the compound. In another embodiment, the desired in vivo biological activity is achieved by the administration of such polymer-compound adducts less frequently or in lower doses than with the unmodified compound.

In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the particle and/or the composition comprising the particle as described herein described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved.

In one embodiment, the amount of a composition to be administered will, of course, be dependent on the subject being treated, the severity of the affliction, the manner of administration, the judgment of the prescribing physician, etc.

In one embodiment, compositions including the preparation of the present invention formulated in a further compatible pharmaceutical carrier are also be prepared, placed in an appropriate container, and labeled for treatment of an indicated condition.

In one embodiment, compositions of the present invention are presented in a pack or dispenser device, such as an FDA approved kit, which contain one or more, unit dosage forms containing the active ingredient. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

Delivery Methods

According to some embodiments of the present invention, there is provided a method of delivering an agent to the gastrointestinal tract of a subject, comprising the step of administering to the subject a nutritionally or a therapeutically effective amount of the composition described herein. In some embodiments, the delivering is to a location selected from a distal gut or a colon of the subject. In some embodiments, the agent is a therapeutic agent. In some embodiments, the agent is a prebiotic nutritional agent. In some embodiments, the agent is a prebiotic growth factor.

In some embodiments, the prebiotic carbohydrate forming the corona of the particles of this invention have increased affinity or specificity or selectivity to transporters or other membrane proteins of a population of probiotic bacteria.

In some embodiments, the population of probiotic bacteria being targeted using the particles and compositions of the invention comprise at least one species selected from lactobacilli and bifidobacteria. Additional non-limiting examples of targeted probiotic bacteria include probiotic enterococcus, lactococcus and any other probiotic bacteria typically residing in the gastrointestinal tract of a human (or a pet or an animal such as of agricultural significance), and specifically distal gut and/or colon.

In some embodiments, the carbohydrate described herein is resistant to degradation/absorption by the human gastrointestinal system. In some embodiments, the carbohydrate is selectively bound by a probiotic bacterium in a human colon. In some embodiments, the carbohydrate is metabolized by a probiotic bacterium in a human colon. In some embodiments, carbohydrate covalent linking to a protein prevents the absorption of the protein in the small intestine.

According to some embodiments of the present invention, there is provided a method of enriching probiotic bacteria in the colon of a subject, comprising the step of administering to the subject a nutritionally or a therapeutically effective amount of the composition described herein.

Techniques for formulation and administration of drugs are found in "Remington's Pharmaceutical Sciences," Mack Publishing Co., Easton, Pa., latest edition, which is incorporated herein by reference.

In one embodiment, suitable routes of administration, for example, include oral, rectal, or intestinal delivery.

In some exemplary embodiments, the protein described herein is lactoferrin. In some embodiments, the lactoferrin further possesses anti-bacterial activity. In some embodiments, lactoferrin further possesses anti-viral activity. In some embodiments, lactoferrin further possessing an anti-fungal activity.

In some embodiments, the composition described herein is used for a targeted protein and/or growth factor delivery to a probiotic bacterium in a human colon.

The Process

According to some embodiments of the present invention, there is provided a process for producing the particle described herein, the process comprises the steps of: (a) covalently bonding a protein and a prebiotic carbohydrate, thereby forming a conjugate; and (b) crosslinking at least two conjugates via the carbohydrate. In some embodiments, the covalently bonding comprises contacting the protein and the carbohydrate in an aqueous solution, and incubating the solution for 0.5-5 h at 40-100° C. In some embodiments, the covalently bonding comprises contacting the protein and the carbohydrate in an aqueous solution, drying the solution, thereby forming a powder; and incubating the powder at 50-70° C. at 75-85% relative humidity for 1-72 h. In some embodiments, the crosslinking comprises providing the conjugate, adding a crosslinking compound at a pH solution of at least 8, and incubating the solution for 1-12 h at 20-50° C. In some embodiments, the crosslinking compound is selected from, without being limited thereto, sodium trimetaphosphate (STMP), monosodium phosphate (SOP), sodium tripolyphosphate (STPP), and phosphoryl chloride (POCL₃), or any combination thereof.

In some embodiments, the crosslinking compound weight content, in solution of step (d), is in the range of 1% to 10%. In some embodiments, the crosslinker weight content is 1%, 2%, 3%, 4%, 5%, 6%, 7%, 8%, 9%, or 10%, including any value and range therebetween.

In some embodiments, step (a) is performed at a pH value range of 4 to 11, including any value and range therebetween. In some embodiments, step (a) is performed at a pH value range of 8 to 11, including any value and range therebetween. In some embodiments, step (a) is performed at a pH value of 4, 5, 6, 7, 8, 9, 10, or, 11, including any value and range therebetween. In some embodiments, step (a) is performed at a pH value of 8, 8.5, 9, 9.5, 10, 10.5, or 11, including any value and range therebetween. In some embodiments, step (a) is performed at a pH value of at least 10.

In some embodiments, the process comprises a step of hydrolyzing the protein prior to forming the conjugate, comprising: (i) contacting the protein with a protease in an aqueous solution, and (ii) incubating the solution for 0.5-5 h at 25-45° C. In some embodiments, the hydrolysate is produced by an enzymatic hydrolysis or a chemical hydrolysis. In some embodiments, the protein is a hydrolysate of a protease selected from a gastric protease or an intestinal protease, or any combination thereof. In some embodiments, the proteolytic enzyme is selected from, without being limited thereto, pepsin, rennin, trypsin, and chymotrypsin, or any combination thereof.

In some embodiments, the process comprises a step of activating the protease, comprising (a) incubating the solution of step (i) at pH 1-3, thereby activating the gastric enzyme, and (b) elevating pH to 6-8, thereby activating the intestinal enzyme.

In some embodiments, the process further comprises a step of entrapping an agent selected from, without being limited thereto, a prebiotic growth factor, a nutraceutical, a prebiotic nutritional agent, or a therapeutic agent, or any combination thereof, comprising: contacting the compound with the conjugate prior to step (b) described herein.

In some embodiments, the weight ratio of the protein to the carbohydrate in the solution of step (a) is in the range of 1:10 to 10:1, respectively. In some embodiments, the weight ratio of the protein to the carbohydrate in the solution of step (a) is in the range of 1:5 to 5:1, respectively. In some embodiments, the weight ratio of the protein to the carbohydrate in the solution of step (a) is in the range of 1:2 to 2:1, respectively.

General

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

It should be understood that the terms "a" and "an" and "one" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, "comprise," "include" and "have" and conjugates thereof, are used to indicate that the object or objects of the verb are not necessarily a complete listing of components, elements or parts of the subject or subjects of the verb.

Other terms as used herein are meant to be defined by their well-known meanings in the art.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

EXAMPLES

Various embodiments and aspects of the present invention as delineated hereinabove and as claimed in the claims section below find experimental support in the following examples. Reference is now made to the following examples, which together with the above descriptions illustrate some embodiments of the invention in a non-limiting fashion.

Materials and Methods

Carbohydrate Analysis by High-Performance Anion Exchange Chromatography with Pulsed Amperometric Detection (HPAEC-PAD)

Monosaccharide and disaccharide quantification in the original and dialyzed GOS powders was carried out by high-performance anion-exchange chromatography with pulsed amperometric detection (HPAEC-PAD) (Dionex LC30, Sunnyvale, Calif.) with a pulsed amperometric detector (ED40) and a PAl column. HPAEC-PAD was performed with eluent A (150 mM NaOH) and eluent B (150 mM NaOH and 500 mM sodium acetate). The elusion program: 0-1 min, isocratic elution using 100% A; 1-50 min, linear gradient to 0% A and 100% B. The elution rate was 1 ml/min. Analytical grade glucose and lactose were used as standards.

Conjugation Process by the Maillard Reaction

A solution of 83 mg/ml of lactoferrin and 630 U/ml of pepsin (Sigma) was prepared, and the pH was adjusted to 1.5, then it was stirred at 37° C. for 90 minutes. The pH was then raised to 10 with NaOH, and the solution was centrifuged at 4° C., 10,000×g to remove the insoluble peptides. The supernatant was filtered (0.45 μm, Thermo Scientific), resulting in LFH solution.

A solution of 250 mg/ml GOS was dialyzed in dialysis tubing with a MWCO of 500-1000 Da (Spectrum Laboratories, Inc.) against DW for 24 hours. The retained solution was lyophilized, then reconstituted to obtain a 200 mg/ml aqueous solution, and the pH was raised to 10 with NaOH. The purity of the final GOS used was >95% (analyzed by HPAE-PAD).

The LFH solution was mixed into the GOS solution (final concentrations: 39.6 mg/ml LFH and 105.5 mg/ml GOS). The sample was stirred in a water bath at 70° C. for 50 minutes at a constantly adjusted pH=10. The pH was lowered to 7 with HCl to stop the reaction and the solution was dialyzed against distilled water in dialysis tubing with a MWCO of 2 kDa (Spectrum Laboratories, Inc.) to remove unconjugated GOS. The retained solution was lyophilized.

Estimation of the Extent of Conjugation by o-Phthaldaldehyde (OPA) Assay

The extent of conjugation of GOS to LFH was estimated by the OPA assay. 100 ml of OPA reagent (Sigma) were prepared: 80 mg OPA were dissolved in 2 ml ethanol and added to 0.1 M sodium tetra borate pH 9.5 buffer. 5 ml of 20% SDS, 200 μl of 2-mercaptoethanol and 42.8 ml distilled water were added. 40 μl of sample were added to 1600 μl OPA reagent and gently mixed. After 2 minutes the absorbance at 340 nm was recorded (Ultrospec 3000, GE Healthcare).

Sodium Dodecyl Sulfate Polyacrylamide Gel Electrophoresis (SDS-PAGE) Analysis

The Maillard conjugation progression, and later, the simulated digestion profiles of Maillard conjugates were performed via SDS-PAGE. 20% acrylamide gels were loaded with 50 μg digested protein samples, or 13 μg undigested protein samples. Electrophoresis was performed, gels were fixed, rinsed in DW and stained with Coomassie Brilliant Blue R-250, washed and destained before imaging.

Total Carbohydrate Quantitation by Phenol-Sulfuric Acid Method

The carbohydrate content in the LFH-GOS Maillard conjugates was estimated according to the phenol-sulfuric acid method in a microplate format described previously (Masuko et al., 2005). Briefly, a calibration curve of glucose was prepared with DW (0-0.15 mg/ml). 50 μl of sample were placed in wells of a 96-well microplate. 150 μl of concentrated sulfuric acid were added rapidly, and immediately 30 μl of a 5% phenol (w/v in DW) solution were added. The microplate was floated in a 90° C. water bath for 5 min. The plate was cooled and absorbance at 490 nm was measured (BioTek EON plate reader, Vermont, USA).

Protein Quantitation by the Lowry Method

The protein content in the LFH-GOS Maillard conjugates was estimated according to the Lowry method (Lowry, Rosebrough, Farr, & Randall, n.d.). 100 μl of 2 N NaOH were added to 100 μl of sample. The solution was hydrolyzed at 100° C. for 10 min. After cooling, 1 ml of complex-forming reagent (100:1:1 of 2% sodium carbonate, 1% copper(II) sulfate pentahydrate, 2% sodium potassium tartrate) was added. The solution remained at RT for 10 min. 100 μl of 1 N Folin-Ciocalteu's reagent was added and vortexed. The mixture remained at room temperature for 30-60 min and the absorbance was read at 750 nm (BioTek EON plate reader, Vermont, USA). Concentration was determined via a standard curve of 0-0.5 mg/ml bovine serum albumin (Sigma).

Conjugate Durability by Simulated Static In-Vitro Digestion

The durability of the LFH-GOS Maillard conjugates to digestion was determined by simulated static in vitro digestion as previously described (Minekus et al., 2014). Briefly, in the gastric phase 1.2 ml of simulated gastric fluid (SGF) stock concentrated ×1.25 were added to a sample of 1.5 ml LFH-GOS Maillard conjugates. The remaining 0.3 ml contained 200 μl of pepsin (P7000, Sigma) in 0.1 M HCl (final concentration 2000 U/ml) were added. The solution was adjusted to pH 3 with HCl and the volume was completed to 0.3 ml with water. The solution was stirred for 2 hours at 37° C. at a constant pH=3. In the intestinal phase, 2 ml of simulated intestinal fluid (SIF) stock concentrated ×1.25 were added to 2.5 ml gastric digesta. The remaining 0.5 ml added, contained 1 M NaOH to raise the pH to 7, trypsin and chymotrypsin (trypsin: T0303; chymotrypsin: C4129, Sigma) at final concentrations of 100 and 25 U/ml, respectively, 134.4 μl of 100 mg/ml taurocholic acid sodium salt hydrate, 117.9 μl of 100 mg/ml sodium glycodeoxycholate, and water to complete the volume to 0.5 ml. The solution was stirred for 2 hours at 37° C. at a constant pH=7.

Particle Sizing by Dynamic Light Scattering (DLS)

Light scattering measurements were performed on a VASCO-2 particle size analyzer (Cordouan Technologies). 100 μl samples of conjugates in PBS (pH 2.8 and pH 6.7) were introduced into the cell at room temperature. Analysis of the data was performed using the nanoQ software (Cordouan Technologies).

*Lactobacillus casei* Growth Procedure for Conjugates Utilization Analysis

Modified MRS broth containing no carbon and no amino acid source (MRS-CP) was prepared. The broth contained 2 gr/L dipotassium hydrogen phosphate, 3 gr/L sodium acetate anhydrous, 2 gr/L triammonium citrate, 0.2 gr/L magnesium sulfate heptahydrate and 0.05 gr/L manganese sulfate tetrahydrate.

The MRS-CP broth was supplemented with 20 gr/L LFH-GOS conjugates powder (consisting 5 gr/L GOS and 15 gr/L LFH), that had undergone simulated static in vitro digestion, as previously described (in bacterial growth experiments, bile salts were not used as they inhibited bacterial growth, and in vivo are mostly re-absorbed in the intestine). A negative growth control was MRS-CP broth supplemented with water that had undergone the same simulated digestion process, instead of the LFH-GOS conjugates powder.

*L. casei* isolates were grown for 48 hours in commercial MRS broth. They were then inoculated in MRS-CP broth at an initial OD600 value of 0.1. Growth was monitored using a microplate spectrophotometer at 37° C. for 72 hours, reading absorbance at 600 nm. Experiments were performed in triplicate.

Evaluation of the Effect of Conjugation on *Lactobacillus casei* Growth

Modified MRS broth containing no carbon source (MRS-C) was prepared. The broth contained 4 gr/L yeast extract, 2 gr/L dipotassium hydrogen phosphate, 3 gr/L sodium acetate anhydrous, 2 gr/L triammonium citrate, 0.2 gr/L magnesium sulfate heptahydrate and 0.05 gr/L manganese sulfate tetrahydrate.

The MRS-C broth was supplemented with 20 gr/L LFH-GOS conjugates powder, or unconjugated LFH and GOS at the same amounts, that had undergone simulated static in vitro digestion, as described above. *L. casei* isolates were grown for 48 hours in commercial MRS broth. They were then inoculated in MRS-C broth at an initial OD600 value of 0.1. Growth was monitored using microplate spectrophotometer as described above.

Example 1: Formation and Characteristics of an LFH-GOS Conjugate

As a non-limiting example, galacto-oligosaccharides (GOS) were selected as the model indigestible prebiotic carbohydrate, and lactoferrin was selected as the model protein. GOS are prebiotic carbohydrates synthesized from lactose, and are most commonly used in infant formulas. They are resistant to degradation in the human gastrointestinal tract by human digestive enzymes, but are metabolized by probiotic colon bacteria to lactate, short chain fatty acids (SCFAs), $CO_2$ and $H_2$. In a large number of human studies with consistent results, consumption of GOS led to selective stimulation of the health-beneficial bifidobacteria and lactobacilli- and supplementation of infant formula with GOS led to fecal abundance of those probiotics comparable to that of breast-fed infants (as human milk naturally contains large amounts of prebiotic oligosaccharides). In some in vitro studies, it was concluded that consumption of GOS may contribute to blocking the adherence of pathogens to the host gastrointestinal epithelial cells. GOS consumption may also enhance calcium absorption due to the reduction in pH caused by the formation of short chain fatty acids (SCFAs) in the colon, increasing calcium solubility and thus improving its absorption. GOS are considered GRAS (Generally Recognized as Safe) by the US FDA for various food categories, and in the European Union GOS can be used as a non-"Novel Food" ingredient in food products.

Lactoferrin (LF) is a natural protein found mostly in milk and whey. LF has been granted GRAS status by the US FDA and is added to commercial infant formula in some countries. Several of LF's known benefits include infection prevention, enhancement of early mucosal gut development and decrease of respiratory and gastrointestinal morbidity. LF also decreases gut colonization by parasites while promoting a bifidogenic microflora in the gut in neonates and preterm babies. In the stomach, pepsin digests LF to peptides. LF hydrolyzed by pepsin (LFH) was found to inhibit pathogens such as *Escherichia coli* and *Staphylococcus aureus* at concentrations of 16 and 8 mg/ml, respectively, while not inhibiting the growth of the beneficial lactobacilli and bifidobacteria under concentrations of ~64 mg/ml. LF peptides are *lactobacillus* and bifidobacteria growth factors, and therefore their use as part of the vehicle for delivery to the colon could be beneficial, (and even synergistic with the oligosaccharides), to both the probiotic bacteria and to the human host.

By conjugating LFH to GOS the proteolysis (and consequently the absorption) of the LFH peptides in the small intestine is suppressed. Moreover, the conjugates can form self-assembled micellar particles whose outer surface is decorated by GOS, thus sterically inhibiting enzyme access, hence degradation of LFH peptides by gastrointestinal enzymes and digestive breakdown of any payload. This would increase the residual amounts of LFH and other vehicle's components reaching the colon, to be selectively utilized by the probiotic bacteria there.

The formation of the LFH-GOS conjugates is shown in FIG. 1. The remaining free primary amino groups in the LFH, available for covalent conjugation to GOS units via the Maillard reaction, were quantified using the OPA assay. A reduction in free primary amino groups in the LFH is observed, until a plateau is reached after ~50 minutes of reaction time. This indicates that the primary amino groups had covalently bound to GOS via the Maillard reaction. Once the minimal value of free primary amino groups is reached, it is preferable to stop the reaction to prevent the formation of more advanced Maillard reaction products, including brown pigments (melanoidins). The progression of the Maillard conjugation was also monitored via SDS-PAGE (FIG. 1, right pane), in which the protein was stained with Coomassie Blue dye, and GOS remained unstained. This figure shows the molecular weight distribution of the conjugates during the progression of the Maillard reaction. Before the Maillard reaction commenced, the average molecular weight of the LFH was 5.2 kDa (bimodal distribution), and as the Maillard reaction progressed, an upwards smear formed, indicating an increase in molecular weight due to covalent bonding of GOS to the LFH peptides. The molecular weight distribution at the end of the reaction, and after lyophilization and reconstitution, ranged between ~2-20 kDa. As GOS are sugars of various degrees of polymerization, and LFH is also composed of polypeptides of various molecular weights, their addition products are bound to have various molecular weights too. Moreover, several GOS molecules may be bound to each peptide, resulting in a "smeared" band on SDS-PAGE. For the remaining experiments and analyses, the Maillard reaction was carried out at pH 10 and 70° C. for 50 minutes, the conjugates were isolated by dialysis, and the solution was lyophilized before further use. The goal was to characterize the conjugates and their performance in vitro.

The LFH-GOS conjugates powder component quantification, and particle size distribution in buffers of various pH values, is shown in Table 1.

TABLE 1

| LFH-GOS Maillard conjugates powder characterization | | |
| --- | --- | --- |
| Protein content % (W/W) | | 76 ± 1 |
| Carbohydrate content % (W/W) | | 25 ± 4 |
| Volume mean diameter ± standard deviation [nm] | pH 2.8 | 870 ± 380 |
| | pH 6.8 | 370 ± 130 |

The protein-to-carbohydrate ratio was about 3:1. This is presumably the highest amount of GOS that could be bound to the LFH under the aforementioned reaction conditions, as the GOS was in excess in the reaction solution. The pH values of the buffers selected for the particle size distribution analysis (Table 1), 2.8 and 6.8, represent pH values of various food products, such as acidic beverages and milk, respectively. Both samples exhibited multi-modal particle size distributions, with no particular trend in particle size with rising concentration between 0.1-20 mg/ml. This corresponds to the SDS-PAGE results in FIG. 1, in which a wide molecular weight distribution can be seen. As the molecular weights of the Maillard reaction products were highly varied, it expected that they would form self-assembled particles of various sizes. The relatively large particle sizes suggest that the self-assembled particles had formed aggregates. Based on the literature, the minimal particle size that can be detected by the palate is 25 μm. The particle size of the LFH-GOS conjugates in both buffers was under 2 μm, so that they can therefore be added to food and beverages without harming smoothness.

Example 2: In-vitro Simulated Digestion Experiments

An in vitro simulated digestion experiment analyzed by SDS-PAGE (FIG. 2) showed that a significant portion of the protein in the Maillard conjugates survived both gastric and intestinal digestion, and is therefore expected to reach the colon in in vivo experiments as well, and be used by the colonic probiotic bacteria.

A solution of lactoferrin was hydrolyzed by pepsin at pH 2. A solution of galacto-oligosaccharides (GOS) was added to the lactoferrin hydrolysate (LFH) solution and the pH was raised to 10. The solution was heated, while stirring, for 50 minutes at 70° C. and to stop the Maillard reaction, the pH was lowered to 7 and the solution cooled down. The in vitro simulated digestion experiment was performed according to an international-consensus protocol with 2 hours of gastric digestion followed by 2 hours of small intestinal digestion. Materials surviving the entire intestinal phase are assumed to be capable of arriving at the colon. Following simulated digestion, the samples were analyzed by SDS-PAGE, where a band indicates a protein or a peptide, and the position of a band within each lane indicates its molecular weight.

Figure 2:
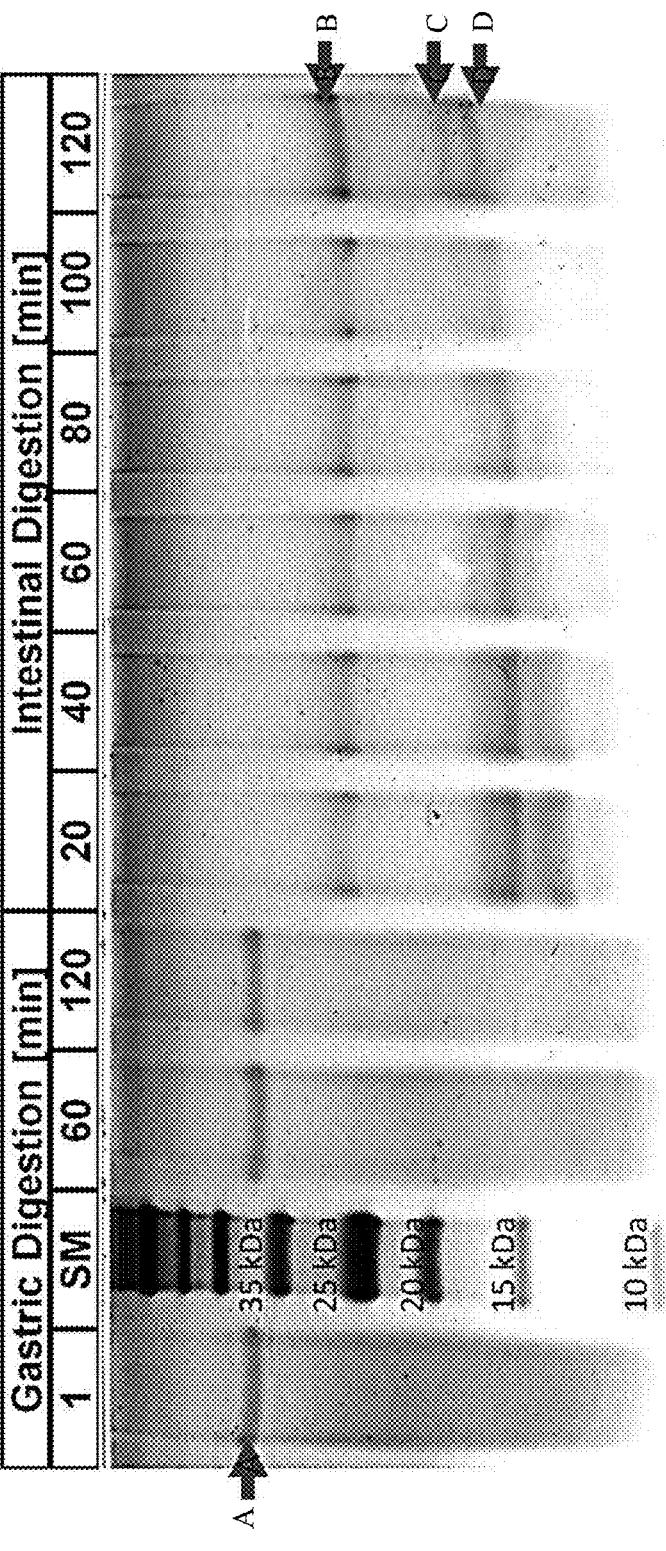
FIG. 2 presents the results of sodium dodecyl-sulphate gel electrophoresis (SDS-PAGE) following in vitro simulated adult-gastrointestinal-digestion of LFH-GOS conjugates. Arrows point to bands of the enzymes trypsin (B,C), chymotrypsin (D) and pepsin (A). SM=molecular weight size marker. The gray smeared band above 10 kDa, remaining almost unchanged during the entire digestion, indicates that most LFH-GOS particles endured gastrointestinal digestion.

FIG. 2 shows the SDS-PAGE analysis of LFH-GOS conjugates during in-vitro simulated adult gastrointestinal digestion. Arrows point to bands of the enzymes trypsin (B,C), chymotrypsin (D) and pepsin (A). SM=molecular weight size marker.

Unprotected proteins are normally digested into small peptides and amino acids during the first minutes of adult intestinal digestion. In the case of the LFH-GOS conjugates, the lane at 1 minute of gastric digestion, which represents the beginning of the simulated digestion, shows a long smear-representing the undigested LFH-GOS conjugates with various molecular weights, ranging predominantly from 10 to 35 kDa but also higher. After 120 minutes of gastric digestion, the long smear seems largely unchanged, indicating that most LFH-GOS particles endured gastric digestion. This result was expected, as the lactoferrin was pre-digested with pepsin prior to conjugation with GOS, and the LFH-GOS particles were thus expected to be resistant to peptic digestion. During intestinal digestion, a slight modification of the LFH-GOS smear can be observed (disregarding the bands of the added enzymes), though by the end of 120 minutes of intestinal digestion a significant amount of smeared band can still be observed.

Conjugation of sugars to proteins via the Maillard reaction reduces the digestibility of the protein. The protein content of the LFH-GOS conjugates was protected from proteolysis during simulated gastrointestinal digestion thanks to pre-digestion with pepsin, and to the conjugation with the indigestible GOS, which also apparently led to conjugate self-assembly with the peptides at the core—hence protected by the corona of the oligosaccharides from further enzymatic digestion by trypsin and chymotrypsin. As a significant portion of the protein in the Maillard conjugates endured both gastric and intestinal digestion, it is expected to reach the colon in in-vivo experiments as well, and be utilized by the colonic probiotic bacteria. In fact, the oligosaccharides, for which probiotic bacteria are believed to have specific transporters are expected to serve as an active targeting mechanism, analogously to selective active targeting to cancer cells, and to be selectively bound by these transporters, expressed uniquely by probiotic bacteria.

Example 3: In-Vitro Utilization of LFH-GOS Conjugates by *L. casei*

*L. casei* was selected as a model probiotic bacterium to evaluate the ability of probiotic bacteria to utilize the LFH-GOS conjugates as a carbohydrate and amino acid source, and to establish the impact of the Maillard conjugation on the ability of probiotic bacteria to utilize LFH-GOS conjugates compared with the utilization of the unconjugated components.

Figure 3:
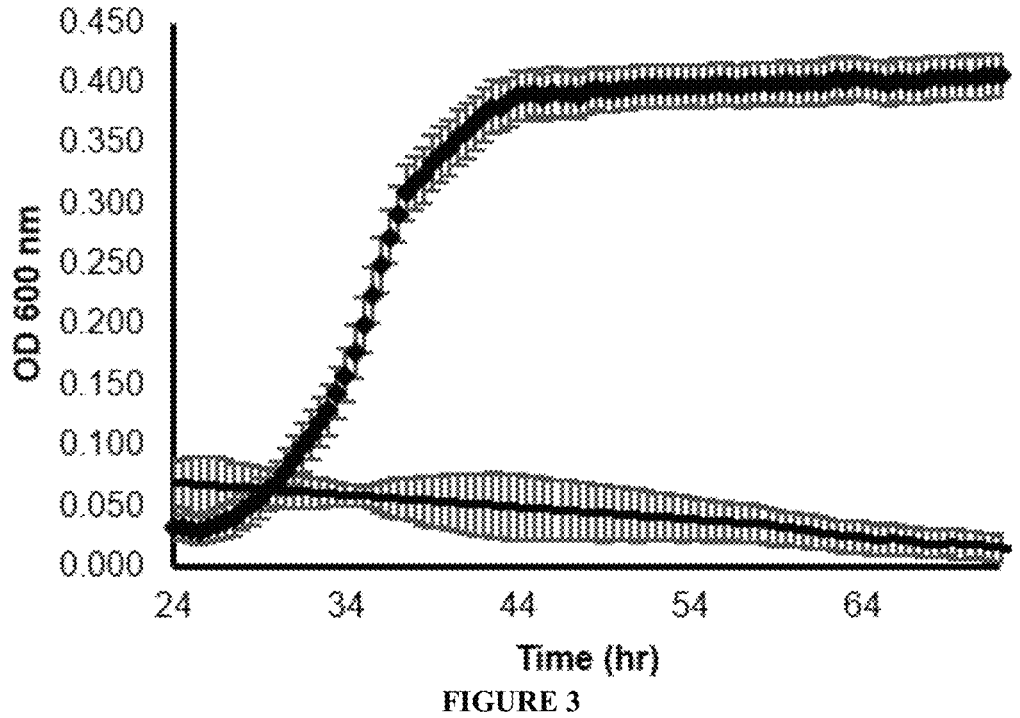
FIG. 3 presents the growth curve of L. casei on a minimal growth medium, plus LFH-GOS conjugates, which had undergone simulated digestion, as the sole carbohydrate and amino acid source (♦). The negative control (–) contained minimal growth medium plus water (in place of the LFH-GOS conjugates) that had undergone simulated digestion.

To simulate the process in the human body, the LFH-GOS conjugates underwent simulated gastrointestinal digestion prior to their addition to the growth medium. The growth curve of *L. casei* on a minimal growth medium containing the digested LFH-GOS conjugates as the sole carbohydrate and amino acid source is shown in FIG. 3.

To evaluate the effect of the Maillard conjugation on the ability of *L. casei* to utilize LFH and GOS as a carbohydrate and amino acid source, *L. casei* were grown on a minimal growth medium containing either LFH-GOS conjugates or unconjugated LFH and GOS at same concentrations as in the conjugate-containing medium. Both samples had undergone simulated gastrointestinal digestion. These growth curves are shown in FIG. 4.

Figure 4:
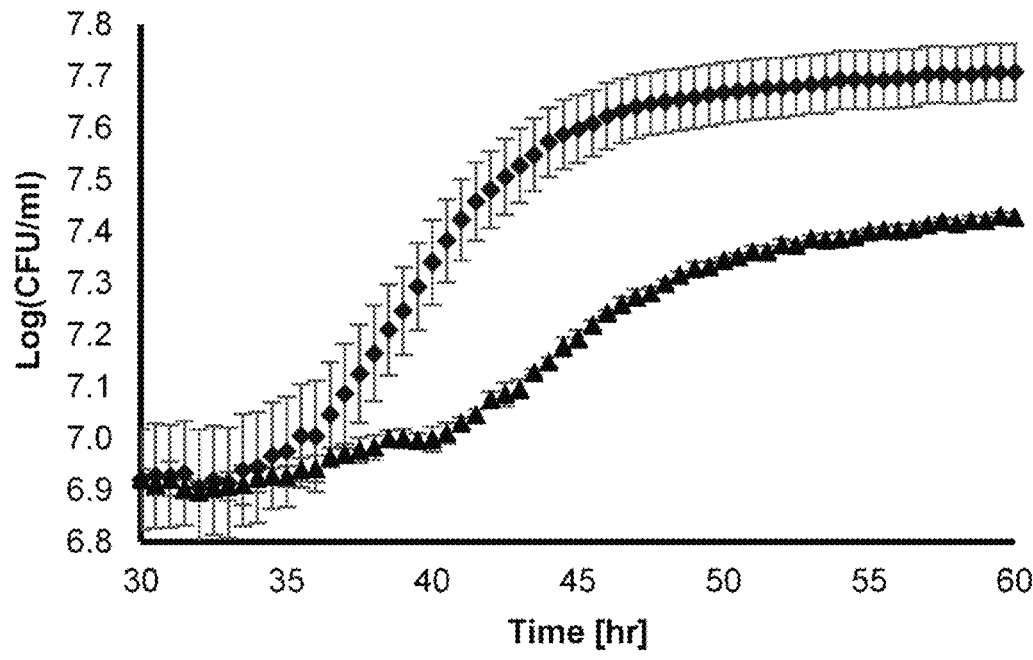
FIG. 4 presents a comparison of L. casei growth on a minimal growth medium containing either LFH-GOS conjugates (♦) or unconjugated LFH and GOS at same respective concentrations (▲) as sole carbohydrate and nitrogen source. Both samples underwent simulated gastrointestinal digestion prior to addition to growth media. The bacterial growth on the conjugates is superior to that on their unconjugated components (growth rates on LFH-GOS conjugates were 2-fold higher compared to the unconjugated components: 0.082 and 0.041 hr$^{-1}$, respectively).

FIG. 4 shows that the Maillard conjugation of GOS to LFH dramatically, and quite surprisingly, improved the ability of *L. casei* to utilize the components compared to unconjugated GOS and LFH (growth rates on LFH-GOS conjugates were 2-fold higher compared to the unconjugated components: 0.082 and 0.041 hr-1, respectively). Presumably, the advantage of the conjugates would be even more pronounced if digestion products are removed by absorption. As previously stated, the protein component of the conjugates was protected during simulated digestion. In the LFH-GOS conjugates sample, at the end of digestion, the protein fraction was mainly comprised of (conjugated) peptides, whereas the protein fraction in the unconjugated components sample underwent complete proteolysis and was comprised of mainly amino acids. Peptides are the preferred substrates for many colonic bacteria due to kinetic advantages of peptide-uptake systems in comparison with those for free amino acids, partially explaining the superior growth rate of *L. casei* on the conjugates. Without wishing to be bound to any mechanism of action, a possible explanation is that transporters on the cell surface of lactobacilli, which are involved in GOS uptake, had bound the GOS fraction and started its uptake. Although transporter specificity would not enable peptide uptake via an oligosaccharide transporter, still the consequent proximity of the GOS-conjugated protein fraction to the bacterium, would facilitate the utilization of the attached protein fraction, by excreted proteases and peptide transporters. Though much is still undiscovered about mechanisms of GOS utilization by probiotic bacteria, lactobacilli have been shown to utilize GOS in two major pathways: the first is transport and phosphorylation by the LacEF system and hydrolysis by the phospho-β-galactosidase LacG, and the second is by transport by LacS, the lactose permease, followed by hydrolysis by (β-galactosidase. It is thus possible that conjugation of GOS to LFH allows selective binding of the LFH-GOS conjugates by probiotic bacteria capable of utilizing GOS, and consequently, these conjugates selectively support the growth and proliferation of these probiotics in the colon by selectively providing them with both carbohydrates and amino acids.

Example 4: A Crosslinked Carbohydrate Particle

Variations of the Maillard conjugates which have the potential to selectively benefit the probiotic bacteria in the colon in-vivo, and be economically attractive, are prepared. Conjugates of lactoferrin digested by pepsin (LFP) and galactooligosaccharides (GOS) with an average degree of polymerization (DP)-5 have been already developed. The conjugation of LFP to different indigestible prebiotic carbohydrates: FOS (DP~10) and inulin (DP~23) is assessed. In order to increase vehicle robustness, cross-linking of the carbohydrate fraction using sodium trimetaphosphate (STMP), an inexpensive food-grade cross-linker used in the starch industry, is examined. Crosslinking should protect the protein from protease accessibility, so that predigestion would not be necessary.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A nutraceutical composition comprising a plurality of particles, each of the plurality of particles comprises a plurality of Maillard conjugates, wherein each Maillard conjugate comprises a peptide covalently bound to a prebiotic carbohydrate, wherein: said peptide is a lactoferrin peptide; wherein said prebiotic carbohydrate is selected from the group consisting of galacto-oligosaccharide, fructo-oligosaccharide, inulin, isomalto-oligosaccharide, soy-oligosaccharide, pectic-oligosaccharide, xylo-oligosaccharide and levan, or any combination thereof; at least one of: (i) a w/w ratio the peptide and the prebiotic carbohydrate within the plurality of Maillard conjugates is between 1:1 and 10:1; and (ii) a percentage of unreacted primary amino groups relative to a total amount of primary amino groups within the peptide is at most 50%; and wherein said particle is a core-shell micelle; and wherein at least 70% by weight of the core constitutes of the peptide and at least 70% by weight of the shell constitutes of the prebiotic carbohydrate; and wherein said nutraceutical composition is an oral dosage form.

2. The nutraceutical composition particle of claim 1, wherein the lactoferrin peptides in said plurality of Maillard conjugates are characterized by an average MW of about 5 KDa.

3. The nutraceutical composition of claim 1, wherein said peptide covalently bound to said prebiotic carbohydrate is via a primary amine of said peptide to a carbonyl of said prebiotic carbohydrate; and wherein the prebiotic carbohydrate has a degree of polymerization (DP) between 2 and 50.

4. The nutraceutical composition of claim 1, wherein said particle comprises at least two covalently linked Maillard conjugates.

5. A nutraceutical composition comprising a plurality of particles, each of the plurality of particles consists of a plurality of Maillard conjugates, wherein each Maillard conjugate comprises a peptide covalently bound to a prebiotic carbohydrate, wherein: said peptide is a lactoferrin peptide and is characterized by water solubility of at least about 8% w/v at a pH of 10; said prebiotic carbohydrate is selected from galacto-oligosaccharide and fructo-oligosaccharide; a w/w ratio between the peptide and the prebiotic carbohydrate within the plurality of Maillard conjugates is between 1:1 and 10:1; a percentage of unreacted primary amino groups relative to a total amount of primary amino groups within the peptide is at most 50%; wherein said particle is a core-shell particle and wherein at least 70% by weight of the core constitutes of the peptide and at least 70% by weight of the shell constitutes of the prebiotic carbohydrate; wherein an average size of said plurality of particles is in the range of 10 nm to 1000 nm; and wherein said nutraceutical composition is an oral dosage form.

6. The nutraceutical composition of claim 1, wherein the average size of said micelle is in the range of 10 nm to 1000 nm.

7. The nutraceutical composition of claim 5, wherein said peptide is obtained via hydrolysis of lactoferrin by a human protease selected from the group consisting of: a gastric protease, an intestinal protease, and any combination thereof.

8. The nutraceutical composition of claim 2, wherein said core comprises at least 80% by weight of said peptide and said shell comprises at least 80% by weight of said prebiotic carbohydrate; and wherein said lactoferrin peptide is obtained via hydrolysis of lactoferrin by a human protease selected from pepsin, rennin, trypsin, and chymotrypsin, or any combination thereof.

9. The nutraceutical composition of claim 2, wherein said core, said shell, or both further comprises any one of: a prebiotic nutritional agent; a therapeutic agent, a nutraceutical, and a prebiotic growth factor.

10. The nutraceutical composition comprising a nutritionally or a therapeutically effective amount of the plurality of particles according to claim 1.

11. The nutraceutical composition of claim 10, wherein said composition is selected from the group consisting of: (i) in the form of an agglomerate of particles; (ii) in the form of a powder; and (iii) a suspension formulated for oral administration.

* * * * *